United States Patent
Avuthu et al.

(10) Patent No.: US 12,076,543 B2
(45) Date of Patent: Sep. 3, 2024

(54) APPARATUS, SYSTEM AND METHOD OF PROVIDING A CONFORMABLE HEATER SYSTEM

(71) Applicant: JABIL INC., St. Petersburg, FL (US)

(72) Inventors: Sai Guruva Reddy Avuthu, St. Petersburg, FL (US); Nabel M. Ghalib, St. Petersburg, FL (US); Mark Edward Sussman, St. Petersburg, FL (US); Arnold Reta, St. Petersburg, FL (US); Samantha Lynn Stevens, St. Petersburg, FL (US); Nathaniel Patrick Richards, St. Petersburg, FL (US); Mary Alice Gill, St. Petersburg, FL (US); Girish Satish Wable, St. Petersburg, FL (US); Ronald Harry Darnell, St. Petersburg, FL (US); Ralph Hugeneck, St. Petersburg, FL (US); Jorg Richstein, St. Petersburg, FL (US)

(73) Assignee: JABIL INC.

( * ) Notice: Subject to any disclaimer, the term of this patent is extended or adjusted under 35 U.S.C. 154(b) by 0 days.

(21) Appl. No.: 18/104,621

(22) Filed: Feb. 1, 2023

(65) Prior Publication Data
US 2023/0173197 A1 Jun. 8, 2023

Related U.S. Application Data

(63) Continuation of application No. 15/829,666, filed on Dec. 1, 2017, now abandoned, which is a
(Continued)

(51) Int. Cl.
*A61M 5/44* (2006.01)
*A61J 1/10* (2006.01)
(Continued)

(52) U.S. Cl.
CPC .............. *A61M 5/445* (2013.01); *A61J 1/10* (2013.01); *G01F 23/263* (2013.01); *G01K 7/021* (2013.01);
(Continued)

(58) Field of Classification Search
CPC ........ H05B 3/342; H05B 3/345; H05B 3/347; H05B 3/36; H05B 1/025; H05B 1/145;
(Continued)

(56) References Cited

U.S. PATENT DOCUMENTS 4,665,304 A   5/1987   Spencer
5,925,275 A   7/1999   Lawson
(Continued)

FOREIGN PATENT DOCUMENTS

CN   1104014   6/1995
CN   101253820   8/2008
(Continued)

OTHER PUBLICATIONS

Office Action (Notice of Allowance and Fees Due (PTOL-85)) dated Feb. 8, 2024 for U.S. Appl. No. 17/718,024 (pp. 1-7).

*Primary Examiner* — Brian W Jennison
(74) *Attorney, Agent, or Firm* — Riverside Law LLP

(57) ABSTRACT

The disclosure is and includes at least an apparatus, system and method for a flexible heater sensor suitable for association with a fluid bag. The apparatus, system and method may include a conformable substrate on a ply of the fluid bag opposite a printed flexible heater; and a matched function ink set, printed onto at least one substantially planar face of the substrate. The matched function ink set forms: at least one conductive layer capable of receiving current flow from at least one power source; and at least one dielectric layer capable of at least partially insulating and at least partially limiting conductivity of the at least one conductive layer;
(Continued)

wherein the matched ink set is matched to preclude detrimental interactions between the printed inks of each of the at least one conductive and dielectric layers, and to preclude detrimental interactions with the conformable substrate; and wherein the at least one conductive layer and the at least one dielectric layer comprise a sensing circuit that senses at least the temperature of fluid within the fluid bag.

19 Claims, 15 Drawing Sheets

Related U.S. Application Data continuation-in-part of application No. 15/689,611, filed on Aug. 29, 2017, now Pat. No. 11,304,263, and a continuation-in-part of application No. 15/683,437, filed on Aug. 22, 2017, now abandoned.

(51) Int. Cl.
    *G01F 23/263* (2022.01)
    *G01K 7/02* (2021.01)
    *G01K 13/00* (2021.01)
    *H05B 1/02* (2006.01)
    *H05B 3/14* (2006.01)
    *H05B 3/34* (2006.01)

(52) U.S. Cl.
    CPC ............ *G01K 13/00* (2013.01); *H05B 1/025* (2013.01); *H05B 3/145* (2013.01); *H05B 3/34* (2013.01); *A61M 2205/36* (2013.01); *G01F 23/268* (2013.01); *H05B 2203/002* (2013.01); *H05B 2203/013* (2013.01); *H05B 2203/021* (2013.01); *H05B 2203/036* (2013.01)

(58) Field of Classification Search
    CPC ............... H05B 3/34; H05B 2203/036; H05B 2203/013; H05B 2203/002; A61M 5/445; A61M 2205/36; A61J 1/10
    See application file for complete search history.

(56) References Cited

U.S. PATENT DOCUMENTS

| | | | |
|---|---|---|---|
| 6,055,722 A | 5/2000 | Tighe | |
| 6,142,974 A | 11/2000 | Kistner | |
| 6,235,047 B1 | 5/2001 | Augustine | |
| 6,884,965 B2 | 4/2005 | Nelson | |
| 8,084,722 B2 | 12/2011 | Haas | |
| 9,657,963 B2 | 5/2017 | Lazanja | |
| 9,877,526 B2 | 1/2018 | Haas | |
| 10,201,935 B2 | 2/2019 | Augustine | |
| 2002/0153367 A1 | 10/2002 | Haas | |
| 2005/0007406 A1* | 1/2005 | Haas | H05B 3/84 |
| | | | 347/17 |
| 2005/0115956 A1 | 6/2005 | Wong | |
| 2005/0244587 A1 | 11/2005 | Shirlin | |
| 2006/0060576 A1* | 3/2006 | Haas | A61F 7/007 |
| | | | 219/543 |
| 2006/0119874 A1 | 6/2006 | Kurihara | |
| 2006/0159899 A1 | 7/2006 | Edwards | |
| 2008/0083721 A1* | 4/2008 | Kaiserman | H05B 3/342 |
| | | | 219/211 |
| 2008/0135408 A1 | 6/2008 | Sjolander | |
| 2009/0047008 A1* | 2/2009 | Straley | A01K 63/065 |
| | | | 392/503 |
| 2009/0291604 A1 | 11/2009 | Park | |
| 2010/0140673 A1 | 6/2010 | Daniel | |
| 2011/0117705 A1 | 5/2011 | Samples | |
| 2011/0194846 A1 | 8/2011 | Wang | |
| 2013/0228562 A1 | 9/2013 | Chen | |
| 2013/0248226 A1 | 9/2013 | Sime | |
| 2014/0109667 A1* | 4/2014 | White | G01F 23/243 |
| | | | 73/304 C |
| 2014/0222121 A1 | 8/2014 | Spence | |
| 2014/0263265 A1 | 9/2014 | Augustine | |
| 2015/0250420 A1* | 9/2015 | Longinotti-Buitoni | A61B 5/1135 |
| | | | 600/534 |
| 2015/0366367 A1 | 12/2015 | Augustine | |
| 2017/0239404 A1 | 8/2017 | Shavit | |

FOREIGN PATENT DOCUMENTS

| | | |
|---|---|---|
| CN | 102123561 | 7/2011 |
| CN | 103763956 | 4/2014 |
| CN | 105188164 | 12/2015 |
| CN | 105979616 | 9/2016 |
| CN | 206333390 | 7/2017 |
| CN | 107006074 | 8/2017 |
| EP | 3068189 | 9/2016 |
| KR | 20070000597 | 5/2007 |
| KR | 20120110932 | 10/2012 |
| KR | 101376107 | 3/2014 |
| WO | 2016060838 | 4/2016 |

* cited by examiner

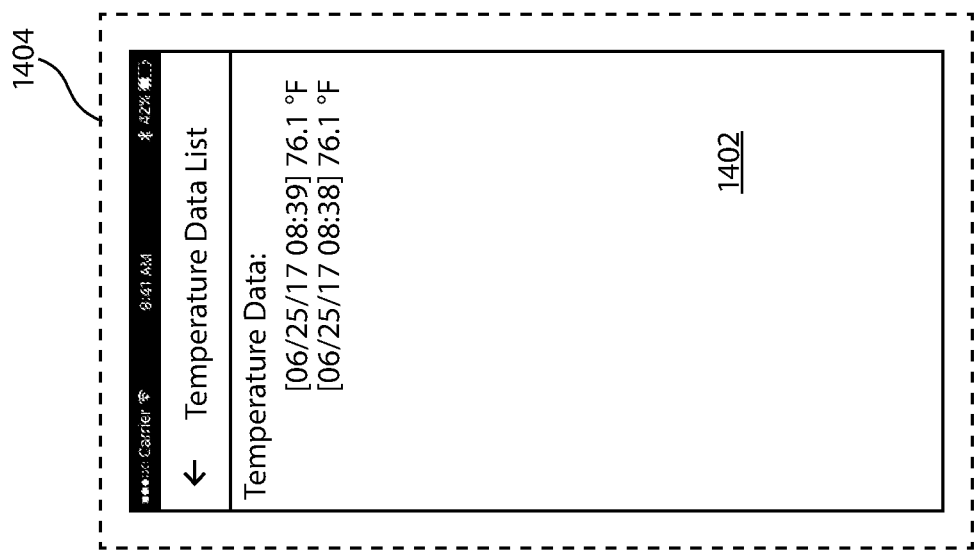
FIG. 14C
FIG. 14B
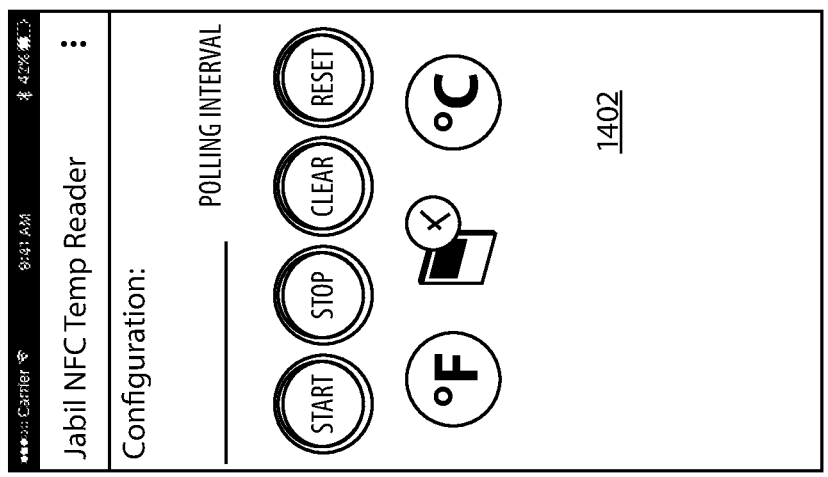
FIG. 14A

APPARATUS, SYSTEM AND METHOD OF PROVIDING A CONFORMABLE HEATER SYSTEM

CROSS-REFERENCE TO RELATED APPLICATIONS

This application is a continuation application of U.S. application Ser. No. 15/829,666, entitled: APPARATUS, SYSTEM AND METHOD OF PROVIDING A CONFORMABLE HEATER SYSTEM, filed Dec. 1, 2017, which is a Continuation-In-Part Application of U.S. application Ser. No. 15/683,437, entitled APPARATUS, SYSTEM AND METHOD OF PROVIDING A FLUID BAG HEATER, filed on Aug. 22, 2017 and U.S. application Ser. No. 15/689,611, entitled APPARATUS, SYSTEM AND METHOD OF PROVIDING A CONFORMABLE HEATER IN WEARABLES, filed on Aug. 29, 2017, the entireties of which are incorporated herein by reference.

BACKGROUND

Field of the Disclosure

The disclosure relates generally to printed electronics and, more particularly, to a conformable heater, such as for use in wearables.

Description of the Background

Printed electronics uses printing, or "additive," methods to create electrical (and other) devices on various substrates. Printing typically defines patterns on various substrate materials, such as using screen printing, flexography, gravure, offset lithography, and inkjet. Electrically functional electronic or optical inks are deposited on the substrate using one or more of these printing techniques, thus creating active or passive devices, such as transistors, capacitors, resistors and inductive coils.

Printed electronics may use inorganic or organic inks. These ink materials may be deposited by solution-based, vacuum-based, or other processes. Ink layers may be applied one atop another. Printed electronic features may include be or include semiconductors, metallic conductors, nanoparticles, nanotubes, etc.

Rigid substrates, such as glass and silicon, may be used to print electronics. Poly(ethylene terephthalate)-foil (PET) is a common substrate, in part due to its low cost and moderately high temperature stability. Poly(ethylene naphthalate)-(PEN) and poly(imide)-foil (PI) are alternative substrates. Alternative substrates include paper and textiles, although high surface roughness and high absorbency in such substrates may present issues in printing electronics thereon. In short, it is typical that a suitable printed electronics substrate preferably has minimal roughness, suitable wettability, and low absorbency.

Printed electronics provide a low-cost, high-volume volume fabrication. The lower cost enables use in many applications but generally with decreased performance over "conventional electronics." Further, the fabrication methodologies onto various substrates allow for use of electronics in heretofore unknown ways, at least without substantial increased costs. For example, printing on flexible substrates allows electronics to be placed on curved surfaces, without the extraordinary expense that the use of conventional electronics in such a scenario would require.

Moreover, conventional electronics typically have lower limits on feature size. In contrast, higher resolution and smaller structures may be provided using printed electronics, thus providing variability in circuit density, precision layering, and functionality not available using conventional electronics.

Control of thickness, holes, and material compatibility are essential in printing electronics. In fact, the selection of the printing method(s) used may be determined by requirements related to the printed layers, layer characteristics, and the properties of the printed materials, such as the aforementioned thicknesses, holes, and material types, as well as by the economic and technical considerations of a final, printed product.

Typically, sheet-based inkjet and screen printing are best for low-volume, high-precision printed electronics. Gravure, offset and flexographic printing are more common for high-volume production. Offset and flexographic printing are often used for both inorganic and organic conductors and dielectrics, while gravure printing is highly suitable for quality-sensitive layers, such as within transistors, due to the high layer quality provided thereby.

Inkjets are very versatile, but generally offer a lower throughput and are better suited for low-viscosity, soluble materials due to possible nozzle clogging. Screen printing is often used to produce patterned, thick layers from paste-like materials. Aerosol jet printing atomizes the ink, and uses a gas flow to focus printed droplets into a tightly collimated beam.

Evaporation printing combines high precision screen printing with material vaporization. Materials are deposited through a high precision stencil that is "registered" to the substrate. Other methods of printing may be used, such as microcontact printing and lithography, such as nano-imprint lithography.

Electronic functionality and printability may counterbalance one other, mandating optimization to allow for best results. By way of example, a higher molecular weight in polymers enhances conductivity, but diminishes solubility. Further, viscosity, surface tension and solids content must be tightly selected and controlled in printing. Cross-layer interactions, as well as post-deposition procedures and layers, also affect the characteristics of the final product.

Printed electronics may provide patterns having features ranging from 3-10 μm or less in width, and layer thicknesses from tens of nanometers to more than 10 μm or more. Once printing and patterning is complete, post treatment of the substrate may be needed to attain final electrical and mechanical properties. Post-treatment may be driven more by the specific ink and substrate combination.

Typical heaters for use in wearables, such as in garments or accessories, are manufactured using conventional electronics techniques and manual labor. For example, rigid, thick, and bulky heaters are typically provided, such as in association with printed circuit boards and the like. The wiring that allows for operation of these thick, bulky heaters is typically sewn into the wearables, such as between fabric layers, to enclose the heating elements into the fabrics.

Moreover, less bulky heaters that are fabricated using atypical types of processing are typically expensive, in part because of the complex fabrication steps needed to create such heaters. Hence, these heaters are not applicable for wearable applications. Further, either of the foregoing atypical or conventional types of heaters necessitates an extraordinary level of encapsulation if the wearable associated with the heater is, for example, to be laundered. This is particularly the case if the wearable is to be laundered many times over its life cycle. That is, the limiting factor in the life cycle of the wearable should not be the heater provided in association with the wearable.

Additionally and in an exemplary circumstance, medical bags, such as medical fluid or blood bags, often require heating. Typically in the known art, such heating is provided by an electronic heating hardware unit into which the medical bag must be placed. Accordingly, relatively large and/or substantially immobile equipment constitutes the manner in which heat is provided to medical fluid bags in known embodiments.

Less bulky heaters that are fabricated using atypical types of processing may provide enhanced mobility, but are typically very expensive, in part because of the complex fabrication steps needed to create such heaters, and are generally not highly reliable. Hence, these heaters are not presently applicable for use in heating in wearables or medical bags.

Therefore, less bulky heaters that may be assembled using in-line and/or high throughput processes, such as additive printing processes, and which is thus less complex in its fabrication resulting in more cost-efficient manufacturing, longer use life of the heater and the wearable, and other distinct advantages, is needed. Such a heater should be formed in a thin, less bulky, more conformable and flexible format, and on a moldable substrate, to not only address the foregoing concerns, but also to allow for integration into more diverse types of uses.

Further, presently the characteristics, such as temperature, of a fluid bag, such as a medical fluid bag, are typically monitored using off bag components, such as including a thermocouple to the bag or an infrared gun, by way of nonlimiting example. Such methods, however, may frequently subject the bag to improper temperature measurements because of, for example, human error, environmental or electrical interference between the bag and the temperature reader, component failure due to the need for various additional normal components to make the electrical connection from the bag to the reader, and so on.

Additionally, present methods of indicating the level of fluid in a bag, such as a medical fluid bag, are limited to weight measurements, such as wherein a bag placed on an IV stand pulls down on a hook that is electrically associated with a measurement scale. Such methods of measuring a level of fluid remaining in the bag are highly inaccurate, however, at least because of the possibility of human error, such as someone pulling down on the bag, environmental and/or use factors, such as shaking of the scale hook when the IV stand is moved, the breaking of electrical connections when an IV stand is moved, and so on.

Yet further, in part due to the inaccuracy of temperature and level sensing presently available in conjunction with fluid bags, methods of conveying temperature and fluid level data to one or more interested parties are presently wholly inadequate. For example, the reading on an infrared gun may be inaccurate for the reasons stated above, such as human error wherein equipment or body parts come between the IR gun and the bag. Further, the readout of a scale and attempt to sense fluid level in a bag may require conversion by a human user, or may be inaccurate for all of the foregoing reasons and additionally because of lack of accounting for the weight of the bag itself, by way of example.

Therefore, the need exists not only for improved designs and printing methods to place a heater in association with a fluid bag, such as a medical fluid bag, but additionally for improved methodologies of associating bag characteristic measurements, such as temperature measurement and level sensing, with a fluid bag, and additionally of providing the data logged in association with such temperature sensing and level sensing to one or more interested users.

SUMMARY

Thus, the disclosure provides at least an apparatus, system and method for a flexible heater. The flexible heater comprises a conformable substrate; a matched function ink set, printed onto at least one substantially planar face of the substrate to form at least a conductive layer capable of receiving current flow from at least one power source; a resistive layer electrically associated with the at least one conductive layer and comprising a plurality of heating elements capable of generating heat upon receipt of the current flow; and a dielectric layer capable of at least partially insulating the at least one resistive layer, wherein the matched ink set is matched to preclude detrimental interactions between the printed inks of each of the at least one conductive, resistive and dielectric layers, and to preclude detrimental interactions with the conformable substrate.

The flexible heater may additionally include an encapsulation that at least partially seals at least the conformable substrate having the matched function ink set thereon from environmental factors. The flexible heater may additionally be integrated into the wearable of the conformable substrate having the matched ink set thereon.

The flexible heater may further comprise a driver circuit connectively associated with the at least one conductive layer. The driver circuit may comprise a control system, and wherein an amount of heat delivered by the heating elements is controlled by the control system.

The disclosure also is and includes at least an apparatus, system and method for a flexible heater sensor suitable for association with a fluid bag. The apparatus, system and method may include a conformable substrate on a ply of the fluid bag opposite a printed flexible heater; and a matched function ink set, printed onto at least one substantially planar face of the substrate. The matched function ink set forms: at least one conductive layer capable of receiving current flow from at least one power source; and at least one dielectric layer capable of at least partially insulating and at least partially limiting conductivity of the at least one conductive layer; wherein the matched ink set is matched to preclude detrimental interactions between the printed inks of each of the at least one conductive and dielectric layers, and to preclude detrimental interactions with the conformable substrate; and wherein the at least one conductive layer and the at least one dielectric layer comprise a sensing circuit that senses at least the temperature of fluid within the fluid bag.

Thus, the disclosure provides improved designs and printing methods to place a heater in association with a fluid bag, such as a medical fluid bag, wearables, and additionally for improved methodologies of associating bag characteristic measurements, such as temperature measurement and level sensing, with a fluid bag, and additionally of providing the data logged in association with such temperature sensing and level sensing to one or more interested users.

BRIEF DESCRIPTION OF THE DRAWINGS

The exemplary compositions, systems, and methods shall be described hereinafter with reference to the attached drawings, which are given as non-limiting examples only, in which:

FIGS. 14A-14C are illustrations of exemplary mobile apps for sensor data;

DETAILED DESCRIPTION

Figure 1:
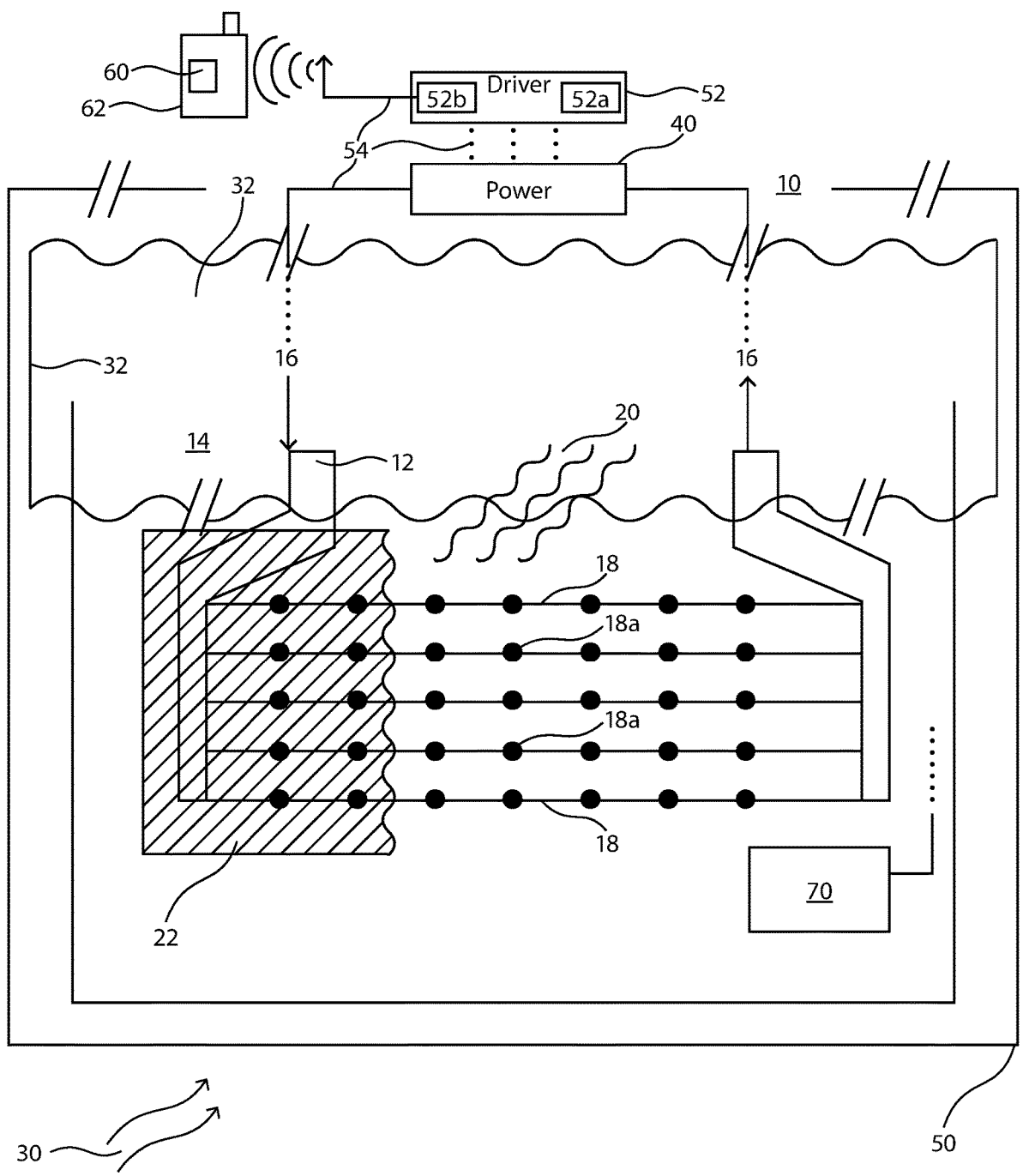
FIG. 1 is a schematic and block diagram illustrating a heater according to the embodiments.

The figures and descriptions provided herein may have been simplified to illustrate aspects that are relevant for a clear understanding of the herein described apparatuses, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, for the sake of brevity a discussion of such elements and operations may not be provided herein. However, the present disclosure is deemed to nevertheless include all such elements, variations, and modifications to the described aspects that would be known to those of ordinary skill in the art.

Embodiments are provided throughout so that this disclosure is sufficiently thorough and fully conveys the scope of the disclosed embodiments to those who are skilled in the art. Numerous specific details are set forth, such as examples of specific components, devices, and methods, to provide a thorough understanding of embodiments of the present disclosure. Nevertheless, it will be apparent to those skilled in the art that certain specific disclosed details need not be employed, and that embodiments may be embodied in different forms. As such, the embodiments should not be construed to limit the scope of the disclosure. As referenced above, in some embodiments, well-known processes, well-known device structures, and well-known technologies may not be described in detail.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

When an element or layer is referred to as being "on", "upon", "connected to" or "coupled to" another element or layer, it may be directly on, upon, connected or coupled to the other element or layer, or intervening elements or layers may be present, unless clearly indicated otherwise. In contrast, when an element or layer is referred to as being "directly on," "directly upon", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). Further, as used herein the term "and/or" includes any and all combinations of one or more of the associated listed items.

Yet further, although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the embodiments.

Historically and as discussed throughout, the formation of many small aspects of devices or small devices has generally integrated the processes of deposition and etching. That is, traces, such as conductive traces, dielectric traces, insulating traces, and the like, which include formation of device features such as wave guides, vias, connectors, and the like, have generally been formed by subtractive processes, i.e., by creating layers which were later etched to remove portions of those layers to form the desired topologies and features of a device.

Additive printing processes have been developed whereby device features and aspects are additively formed, i.e., are formed by "printing" the desired feature at the desired location and in the desired shape. This has allowed for many devices and elements of devices that were previously formed using subtractive processes to be formed via additive processes, including, but not limited to, printed transistors, carbon-resistive heating elements, piezo-elements and audio elements, photodetectors and emitters, and devices for medical use, such as glucose strips and ECG straps.

In short, the printing of such devices is dependent on a number of factors, including matching deposited materials, such as inks, to substrates for particular applications. This ability to use a variety of substrates may afford unique properties to printed devices that was previously unknown in etched devices, such as the ability for devices to stretch and bend, and to be used in previously unknown or inhospitable environments, such as use as conformable heaters in wearables that are to be laundered. By way of non-limiting example, the ability to print electronic traces on plasticized substrates allows for those substrates to be conformed after printing has occurred.

However, known additive properties do present limitations over the properties previously available using subtractive processing. For example, it is typical that conductive traces formed using additive processes have more limited conductivity than the conductive traces previously formed using subtractive processes. This is, in part, because pure copper traces provided using subtractive processes are presently unavailable to be printed using modern additive processing. Accordingly, some devices and elements thereof, such as heaters, may be subjected to substantial modification in order to accommodate the modified properties available using printed traces in additive processes, as compared to the use of conventional electronics-formation techniques.

In the embodiments, a large number of factors must be balanced in each unique application in order to best arrive at properties that most closely approximate those properties previously available only in subtractive processes. For example, in the disclosed devices and processes for creating those devices, compatibility must be assessed as between a substrate for printing and the receptivity of such substrate, the inks employed and the conductivity thereof, the fineness of the printed traces used, the pitch, density and consistency of the printed inks, the type of printing performed, i.e., screen printing versus other types of printing, the thickness of the printed layers, and the like. Moreover, because multiple inks may be employed in order to create the disclosed heating elements, the compatibility of the inks used with one another is also an aspect of the embodiments. For example, chemical reactions between inks, different curing methodologies between inks, and the manner of deposition as between inks must all be assessed for all inks within a given ink set. Also of note, the skilled artisan will appreciate, in light of the discussion herein, that different inks within an ink set may have variable characteristics even after deposition. For example, certain inks may suffer from a valley effect in the center of a deposited trace of that ink, while peaks are created at the outer part of traces using that ink. Accordingly, because the thickness of a trace deposited using such an ink may allow for alleviation or heightening of the foregoing effect, the manner and consistency of application of each ink within an ink set is noteworthy in the embodiments.

In the known art of incorporated heaters, printed circuit boards needed to be mechanically integrated, and hence accounted for, within each product. However, the ability to use printed electronics with flexible substrates and substrates having uneven topologies may allow for printed electronics to be integrated as part of a product, instead of necessitating a mechanical integration of the electronics into the finished product. Needless to say, this may include the use of printed electronics onto substrates unsuitable for accepting electronics created using subtractive processes, such as fabrics, plastics that do not provide "sticky" surfaces, organic substrates, and the like. This may occur, for example, because additive processes allow for different printing types within each subsequently printed layer of the printed device, and thereby the functionality provided by each layer, such as mechanical, electrical, structural, or other functionality, may be varied as between printed layers throughout a deposition process.

Various solutions to balance the foregoing factors may be provided using additive processing. For example, a flexible substrate may be provided, wherein printing occurs on one or both sides of the substrate, such as on one or both sides of a medical bag. Thereby, traces may be produced on one or both sides of the bag to form one heater unit, or series or parallel heaters. In such instances, one or more vias may be created between the sides of the bag, thus producing one heating system, or multiple heat systems on opposing sides of the bag may be connectible through or around the contents of the bag.

The embodiments provide at least a printed heater on a fluid bag substrate, such as a medical grade substrate as may be used for IV fluids, blood bags, or the like, or on a flexible substrate for use in association with a wearable, that is formed of a layer or layers of functional ink(s), such as conductive inks, resistive inks, and insulating inks, formed into traces using additive processes to thereby effectuate the heater unit. Additional printed electronics may also be provided using the same or similar additive processes, such as electronics including sensors, antennas, such as RF, NFC, or the like antennas, thermometers, thermocouples, fluid sensors, and the like.

The embodiments may accordingly provide not only heaters for heating, such as of wearable or of fluid within a bag, but additionally sensors integrated with the bag, such as to allow for traceability, network connectivity, and patient care reporting. This traceability, connectivity, and reporting may be manual or automatic, and may be occasional, periodic, semi-continuous, and/or continuous in accordance with the embodiments. These functionalities may allow for reductions in human error in patient monitoring and reporting, for example.

In accordance with the foregoing, the embodiments provide less bulky heating equipment, such as to allow for optimized conditions in cramped spaces, such as in clothing, or in operating rooms or ambulances. Further, the embodiments provide improved patient care by regulating the heating of medical fluids to ensure the fluids do not under- or overheat and cause patient discomfort, injury, or death. Further, such heaters may provide improved user comfort and ease of use.

Medical bags provide unique impediments to allowing for the use of additive processes, such as the printing of electronics, in association therewith. For example, because a medical bag typically has a texture associated therewith, and is highly resistant to tearing and puncture, and hence is thick and highly flexible in association with the texturing, a medical bag provides a unique substrate for additive processes. Further, a medical bag must be inert in its properties in order to allow for maintenance of sanitary conditions in association with patient care. The disclosed embodiments may be used in association with any such fluid bag, or with any other bag or substrate having such impediments to printing thereon, such as a flexible substrate for inclusion in a wearable. Furthermore, the disclosed embodiments may be used with any substrate of any size or shape.

More particularly, in the embodiments, a flexible heater for use in a wearable or on a fluid bag may be printed onto a flexible and conformable organic or inorganic substrate, such as using a "matched function" ink set. The flexible heater may be comprised of multiple layers of inks or substances forming the matched function set. For example, and as illustrated with respect to the heater 10 of FIG. 1, a conductive layer 12 may be printed onto substrate 14 to allow for current flow 16 to the heater. A resistive layer 18 may also or subsequently be printed to allow for the heating effect 20 to occur upon heating of the resistors due to the current flow 16 therethrough. Further, a dielectric layer 22 may be printed to insulate the resistive elements 18a, both from shorting onto one another because of the conformable, flexible nature of the substrate 14, and to insulate the heat produced by the heating elements 18a to avoid localized overheating.

Of course, the third layer 22 may additionally be provided below or between other layers 12, 18. For example, in a particular exemplary embodiment, a printed heater not including a dielectric layer 106 may be limited in operation to a temperature range of 45 to 50 degrees Celsius; but the same heater including a dielectric layer 22 may be operated in a temperature range of 45 to 65 degrees Celsius without concern that the excessive heat will pass improperly from the heater out into contact with the environment, such as a hand placed on or near a fluid bag 50.

The substrate 14 onto which the layers 12, 18, 22 are printed may include both organic and inorganic substrates, subject to the limitation that substrates may be flexible and/or conformable to the wearable or fluid bag into or onto which the heater 10 is placed. Suitable substrates may include, but are not limited to PET, PC, TPU, nylon, glass, fabric, PEN, and ceramics.

As referenced above, various inks and ink sets may be used to form the layers 12, 18, 22, or aspects thereof, in heater 10, and inks within the set may be matched to one another so as to avoid undesired chemical interactions during deposition, curing, etc., and/or may be matched to the substrate onto which the inks are to be printed. By way of non-limiting example, conductive and resistive inks used may include silver, carbon, PEDOT:PSS, CNT, or a variety of other printable, conductive, dielectric and/or resistive materials that will be apparent to the skilled artisan in light of the discussion herein.

In certain embodiments, particularly those exposed to the elements and/or intended for laundering, or for use in harsh or sterile operating room conditions, the heating system 10 may preferably be encapsulated in order to increase durability. In such cases, isolation from environmental conditions 30, such as wet conditions, including rain, snow, or humidity, and/or insulation from wash and dry cycles and/or general robust handling, may be performed. In such cases, an encapsulation system 32, such as a laminated pouch, may be optionally provided to enclose the heating system 10, and, in such cases, the encapsulation 32 may include connectivity and/or pass-throughs to allow for the provision of power 40 through the encapsulation system 32 to the heating system 10. Finally, the heating system 10, such as including the encapsulation 32, may be integrated into a wearable or bag 50 via any known method, such as by sewing, lamination, or the like.

Thus, encapsulation 32 may provide waterproofing, air-proofing, or the like in order to protect the heating system and associated systems from any adverse environmental factors 30. To provide the encapsulation 32, various known techniques may be employed. For example, acrylics may be laminated onto each side of the heater substrate 14, such as to create a sealed lamination lip around the substrate 14, with the only projections extending therefrom having the acrylic lamination seal therearound. Further, such a laminated pouch may be treated with, for example, ultra-violet radiation such that the lamination is sealed onto, and provides maximum protection of, the heating system 10. Of note however, the more layers that are added to the heating system, such as including encapsulation 32, the less conformable to the wearable the heating system will become, particularly in the case where added layers have significant thickness thereto.

In some embodiments, the encapsulation 32 that protects from environmental conditions 30 may not require any secondary effort beyond production of the heating system 10. For example, substrate and ink combinations may be selected that are submersible and conformable, or only that portion of the substrate having printed electronics thereon to provide the heating system may be sealed, such as with a single acrylic laminate, from environmental conditions.

As referenced above, heating systems 10 with or without encapsulation 32 connect to one or more driving circuits 52. In certain embodiments, interconnection 54 to, for example, driver circuit 52 and/or power 40, may include a high contact surface area, such as to enable the heating system 10 to draw significant current 16 from the power source 40. Also as referenced above, interconnection 54 may also include or comprise printed electronic surfaces. Such interconnections 54 may additionally include classical wiring, micro-connection, and/or electromechanical connection techniques, by way of non-limiting example.

The various interconnections 54, such including those from the driver circuit 52 to external control systems, if any, and/or to the power supply 56, may extend outwardly from the heating system 10. These interconnections 54, as well as data requirements and power requirements, may be dependent on the unique structure of a given heating system 10. For example, different carbon inks applied in the formulation of the heating system 10 may have different power requirements, such as 5-15 volts, or more particularly 5, 9, or 12 volts, by way of non-limiting example.

Similarly, interconnects 54 may also be or include one or more universal connectors known in the art for connectivity to, for example, the aforementioned voltages. Further, such a universal connector may be or include other known connector types, such as USB, micro-USB, mini-USB, lightning connector, and other known interconnects. Additionally and alternatively, proprietary interconnects 54 may be provided in conjunction with the embodiments.

The aforementioned driving circuit 52 may or may not be in direct physical association with the heating system 10 and the interconnects 54. By way of example, the driver circuit 52 may be included as a self-contained system in the electrical pathway between the power source 40 and the heating system 10. The driver circuit 52 may include control systems 52a or connectivity to control systems 52b, such as to allow for remote and/or wireless control of the heating system 10, and/or to provide limitations on the heating system, such as amount of heat delivered, amount of current delivered or power drawn, variation between different heat delivery levels, and the like. Such remote connectivity may include wireless connectivity, such as using NFC, blue tooth, WiFi, or cellular connectivity, such as to link to an app 60 on a user's mobile device 62, by way of non-limiting example.

Of note, the control system(s) 52a, b, such as a Bluetooth-based control system, may allow for a change in temperature automatically or manually, as referenced herein. Accordingly, the control system(s) 52a, b may communicate, such as via Bluetooth, radio-frequency (RF), near-field communications (NFC), or the like, with a secondary controlling device, such as an app on a mobile device or an app or application on a medical monitoring system.

The aforementioned change may occur only for a certain period of time, which may be brief, such as particularly if the control system indicates that significant power will be consumed on a desired setting. For example, it may be manually or automatically selected that a user has pre-set a heater to heat to 85 degrees for 90 seconds, such as only while the user briefly walks a dog outside in 10 degree weather, because it is understood that the user can recharge the system completely immediately after the short-term use. However, if a user is going on a one hour jog, and that jog is in the same 10 degree weather, the user may prefer that the heater operate at 45 degrees for 50 minutes of the hour before the charge is fully consumed.

The power source 40 that delivers power to the heating system 10, such as through the driver circuit 52, may be battery-driven, as mentioned above, if local utility power is not available. The power source in such instances may preferably provide a battery life of, for example, 2-10 hours, or, more specifically, 4-8 hours. This power may be provided, for example, from a permanent power delivery system embedded in a garment or on a bag or IV-fluid pole, such as may use a rechargeable, removable, replaceable, or permanent battery, by way of non-limiting example, or by a secondary power source suitable to be plugged into the driver circuit system, such as may be embedded in or associated with utility-provided power, medical equipment, a mobile device or other mobile power source, via a proprietary or non-proprietary connector, such as via a micro USB, lightning connector, or the like. As referenced, typical power provision elements may include batteries, such as rechargeable batteries, such as lithium ion batteries. Such batteries may typically provide high levels of heating very quickly, and then allow for a quick ramp-down in heat delivery to avoid unnecessary power use during the ramp-up or ramp-down phases of power provision.

Atypical power sources may additionally be used to provide the power source 40 for heating system 10. For example, kinetic power sources, such as those that store power based on movement, and/or other similar magnetic and/or piezo-electric power systems, may be embedded in or connectable to the wearable in order to provide primary, secondary, permanent, or temporary power to the heating system 10 via the driver circuit 52. Likewise, primary, secondary, and/or atypical power source(s) 40 may work together and in conjunction with the aforementioned system control, such as may be embedded in or communicatively associated with the driver circuit 52, to deliver power only upon particular triggers. For example, a wearable equipped with heaters at multiple locations, such as in the elbow of a sweatshirt and in the upper back region, may allow individual ones of those locations to be activated only upon certain events indicated by on-board, such as printed electronic, sensors 70, which may additionally be associated with the substrate 12. For example, a kinetic sensor may sense movement, and during the movement phase may activate a heater in a given location, such as in the upper back region in the prior example. However, upon sensing by the kinetic sensor of the stoppage of movement, the heating element in the elbow of the sweatshirt may be activated. This may be done for any of a variety of reasons understood to the skilled artisan, such as for a pitcher who stops pitching between innings, but wishes to keep his or her elbow "warm" so as to avoid injury.

Such variations in heating elements may not only occur for wearables having multiple heaters, but may similarly include variable heater designs for different purposes. For example, smaller heaters consume appreciably less power than larger heaters, and thus necessitate a lower level power supply. Consequently, in the prior example of a sweatshirt for a pitcher, a small heater located only proximate to the pitcher's "Tommy John" ligament in his or her elbow may require little power for activation, but may nevertheless be enabled to deliver significant health impact to the wearer, such as to keep this oft-injured ligament warm after inactivity of more than 10 minutes has occurred.

Moreover, variability in heat levels, such as may be indicated by the driver circuit system, may be made manually by the user or automatically based on system characteristics. For example, lower levels of heat in a hand warmer heating system, such as may be embedded in the pockets of a sweatshirt or in a user's gloves, may be needed if the temperature is colder, i.e., only a particular temperature differential from environmental conditions may be necessary in order to make a user feel "warm". That is, a user in an environment where the temperature is 10 degrees Fahrenheit may feel much warmer if the user's gloves are warmed to 40 degrees Fahrenheit, rather than warming the gloves all the way to a maximum heating level of 65 degrees. However, in the event the ambient temperature is 35 degrees, the user may need the heating element to go to 65 degrees in order for the user to feel the same level of "warmth".

Additional considerations in power delivered to the heater and/or in the heat delivered may occur based on the use case of the wearable and of the heater. For example, in instances in which the heater might be in substantially direct contact with or very close to the user's skin, the control system associated with the driver circuit 52 discussed herein must limit the power such that the heating is not sufficient to burn, cause discomfort to, or otherwise harm the user. Such concerns may be addressed, in part, through the use of self-regulating inks to provide the heating elements in certain exemplary embodiments.

For example, a positive temperature coefficient (PTC) heater may provide a self-regulating heater. A self-regulating heater stabilizes at a specific temperature as current runs through the heater. That is, as temperature is increased the resistance of the self-regulating heater also increases, which causes reduced current flow and, accordingly, an inability of the heater to continue increasing in temperature. On the contrary, if the temperature is reduced, the resistance decreases, thereby allowing more current to pass through the device. In a typical embodiment, a self-regulating/PTC heater thus provides a stabilized temperature that is independent of the voltage applied to the heater.

Figure 2:
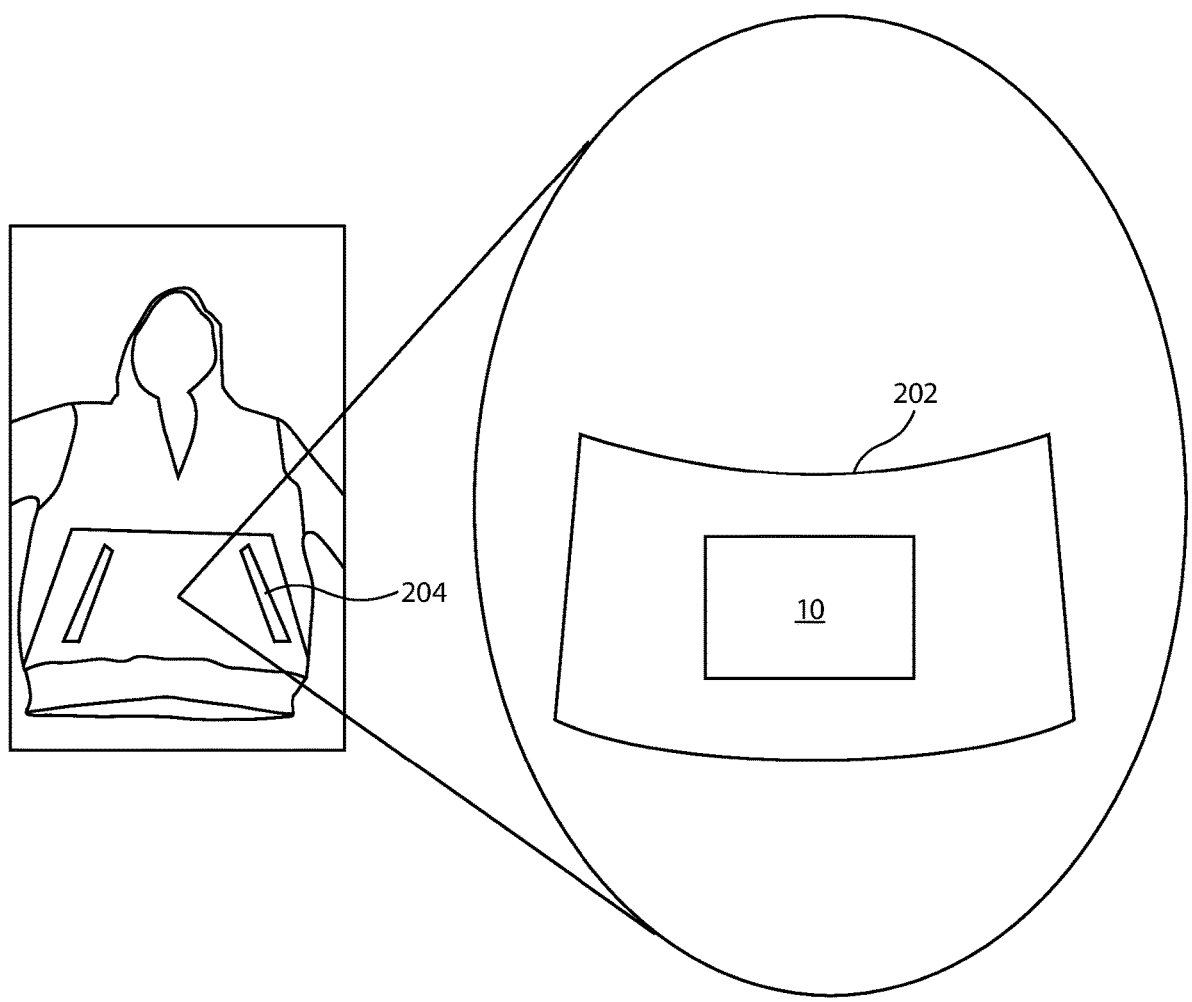
FIG. 2 is a schematic and block diagram illustrating a heater according to the embodiments.

Secondary systems 202 may be provided in conjunction with heating system 10, such as to hold in warmth, as illustrated in FIG. 2. For example, in an embodiment having a laterally crossing pocket 204 in a sweatshirt, the single pocket across the sweatshirt may be lined 202 on the interior portion thereof, and may have the heating element provided interior to the lining of the pocket thereof, in order that the heat generated from the heating system 10 is held within the pocket 204 of the sweatshirt to the maximum extent possible.

As discussed throughout, it may be advantageous, particularly for certain types of wearables or fluid bags, that the heating system and/or the other systems associated therewith be conformable. This conformability may apply to the application of forces by the user or based on the activity, conformance to the physical profile of the wearable/bag itself, or the like. Additional considerations may arise due to the conformability of the heating system and/or its associated systems. For example, delivered heat levels may vary based on the physical configuration of the heating elements, i.e., when the heating system is bent or partially folded, it may deliver greater or lesser heat in certain spots than is anticipated. Needless to say, some of this variability may be accounted for using a protective dielectric layer 22, such as is referenced above.

As discussed throughout, additional sensors, integrated circuits, memory, and the like may also be associated with the discussed heating system 10, may be printed on the substrate 14 thereof, and/or may be formed on or in systems associated therewith, and/or on the substrates thereof. It goes without saying that, in such embodiments, the associated electronics may be discrete from the heating system and those systems associated with the heating system, but may nevertheless be similarly conformable to the wearable, the substrate of the heating system, and so on. Further, those skilled in the art will appreciate that such other electronic circuits may or may not be formed by printing processes on the same substrate, or on a physically adjacent substrate, of the heating system.

Moreover, the embodiments may include additional layers (not shown) to those discussed above. For example, a heater substrate may be provided in the form of a highly adhesive sticker, wherein the sticker may or may not provide a substrate suitable for receiving printed electronics on one side of the "sticker." In such an instance, the compatibly adhesive surface may be applied to the opposing face of the sticker, such as via additive process printing, lamination, deposition, or the like.

Of note, in order to associate the printed electronic layers with a substrate throughout this disclosure, ink sets may be selected in light of process parameters to form the heater and the operation environment in which the bag will be used. For example, not only is application and curing of each ink important in light of the function to be imparted to the bag, but additionally the effects of operating conditions on each ink must be considered. In short, material compatibility must be maintained, and a chemical inertness must be present between the additive process elements. By way of nonlimiting example, the ink solvents used in relation to the inkset may be necessarily inert with respect to both an IV bag, and the sanitary nature and operating environment of the bag. Further, sterilization of the bag using radioactive or ultraviolet processes, if needed, should not degrade the printed electronic materials in the inkset or the functionality provided thereby. Yet further, the surface energy of the substrate must be matched to the applied inks, layers, and/or coatings of the inkset and onto the substrate. Additionally, the curing temperatures of any inks or layers in the inkset must be considered in light of the melting or degradation temperature of the bag itself. For example, bags formed of certain polymers cannot be subjected to heat levels sufficient to cure certain types of frequently used printed electronic inks.

In order to address certain of the foregoing of the concerns and yet obtain sufficient curing of the ink and additive process layers, different types of curing methodologies may be used in the embodiments. For example, convection curing using a convection box or conveyor belt may be used to apply sufficient curing energy; likewise, infrared or near infrared energy may be applied; additionally, ultraviolet curing may be used; and photonic curing may also be employed. Yet further, ramping temperatures may be used in order to provide sufficient levels of curing, such as wherein high or low temperatures are employed to improve the ability of the print substrate to withstand more heat or energy than might otherwise be the case.

Figure 3:
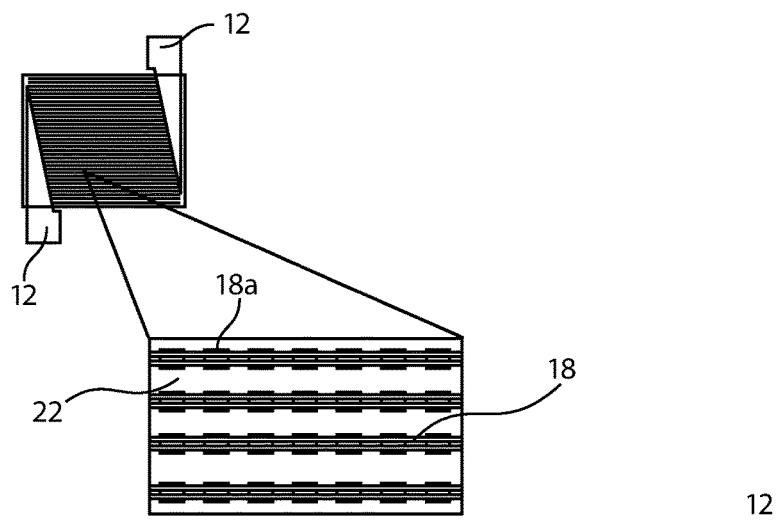
FIG. 3 is an exemplary implementation of the embodiments having a conductor layer with contact points at the top right and bottom left of the heating system.
Figure 4:
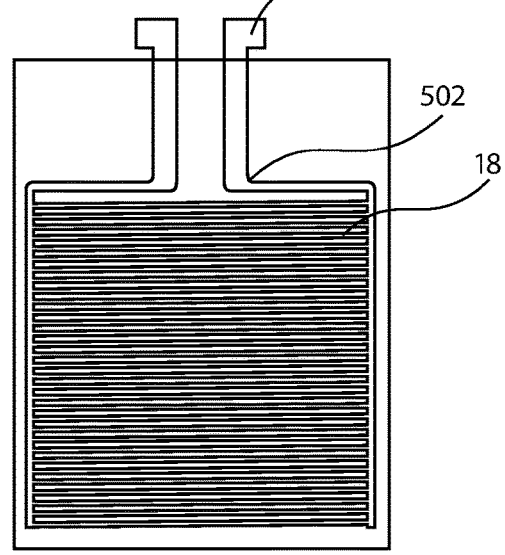
FIG. 4 is an exemplary implementation of a conductive and resistive layer heating system.
Figure 5:
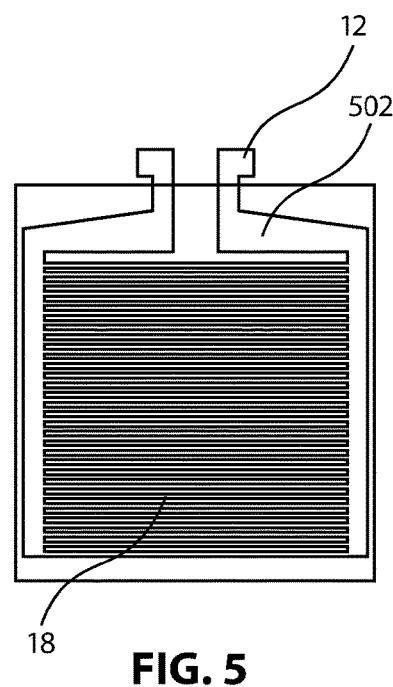
FIG. 5 is an exemplary implementation of an embodiment having an enhanced size of the conductive layer associated with the contact pads at the top of the device.

FIGS. 3, 4, and 5 illustrate exemplary implementations of the disclosed embodiments. More particularly, FIG. 3 illustrates a conductor layer 12 having contact points at the top right and bottom left of the heating system. Further illustrated are discreet heater elements 18a of the resistive layer 18, shown in the blow up of FIG. 3.

FIG. 4 illustrates an additional exemplary implementation of a conductive 12 and resistive layer 18 heating system. FIG. 5 illustrates an additional embodiment, in which the current choke point 502 of FIG. 4 is remedied by enhancements in the size of the conductive layer 12 associated with the contact pads at the top of the device. Of note, each of the embodiments of FIGS. 3, 4, and 5 illustrate a dielectric layer 22 printed over the conductive 12 and resistive layers 18, with the contact points extending beyond the dielectric layer 22 to allow for the interconnections 54 discussed herein.

Figure 6:
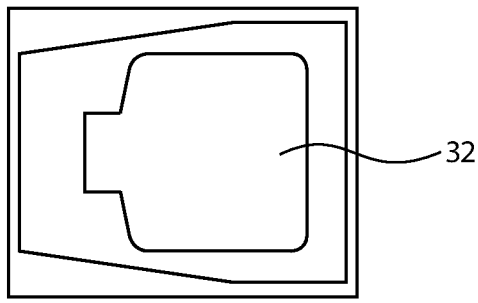
FIG. 6 illustrates an exemplary implementation of a heating system enclosed in an encapsulation layer.

FIG. 6 illustrates an exemplary implementation of the heating system 10 of FIG. 5 enclosed in an encapsulation layer 32. As noted throughout, the encapsulation layer 32 may protect the heating system 10 from environmental conditions.

Figure 7:
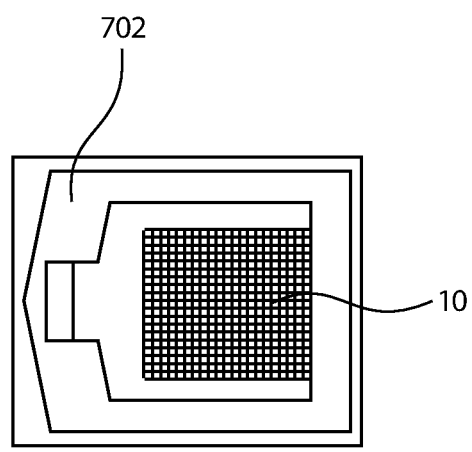
FIG. 7 illustrates an exemplary implementation in which the heating system is laminated to a textile.

FIG. 7 illustrates an exemplary implementation in which the heating system 10 has been laminated to a textile 702. Available textiles may include, by way of non-limiting example, nylons, cottons, or the like.

Figure 8:
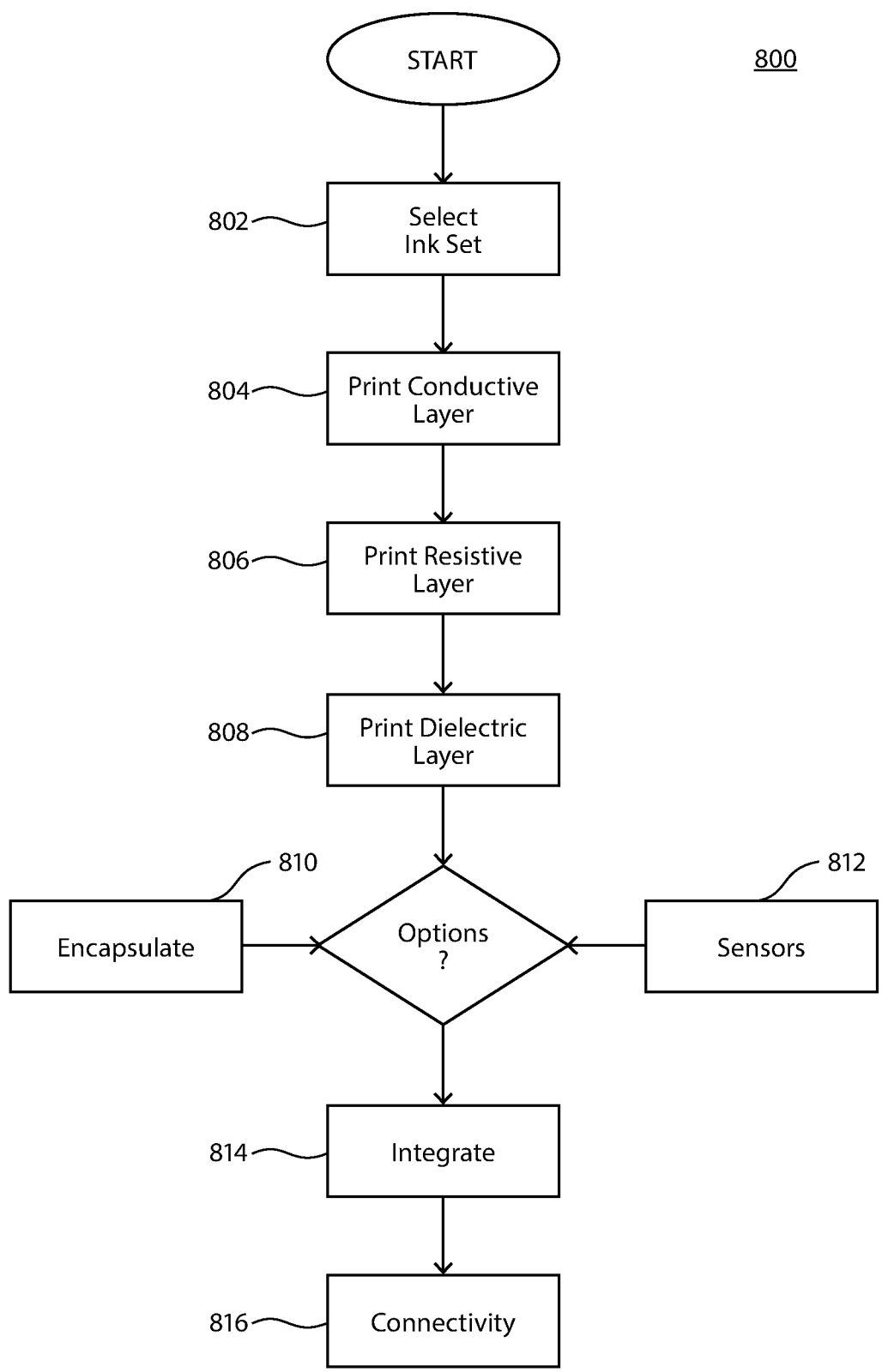
FIG. 8 is a flow diagram illustrating an exemplary method of providing a conformable heater, such as for use in a wearable.

FIG. 8 is a flow diagram illustrating an exemplary method 800 of providing a conformable heater. At step 802, an ink set is inter-matched for use to print compatible ink layers within the ink set, and is matched to a receiving organic or inorganic conformable substrate. At step 804, a conductive layer formed of at least one ink from the ink set is printed on the substrate.

At step 806, a resistive layer is printed from the ink set, wherein the resistive layer provides at least a plurality of heating elements in electrical communication with the conductive layer. At step 808, a dielectric layer is printed from the ink set in order to insulate the conductive and resistive layers.

At optional step 810, the substrate having at least the conductive layer and the resistive layer printed thereon is at least partially encapsulated. At optional step 812, one or more sensors associated with the operation of the heater may be integrated with and/or printed on the substrate.

At step 814, the heater is integrated with a wearable or a bag. Integrating may be by sewing, lamination, adhesion, or any like methodology, including printing upon the bag. Moreover, at step 816, the heater may be connectively associated with one or more driver circuits having control systems communicative therewith, and with one or more power source connections to allow for power to be supplied to the heating elements via the conductive layer. By way of example, step 816 may include the printing or other manner of interconnecting of one or more electrical interconnections to the heater.

Figure 9:
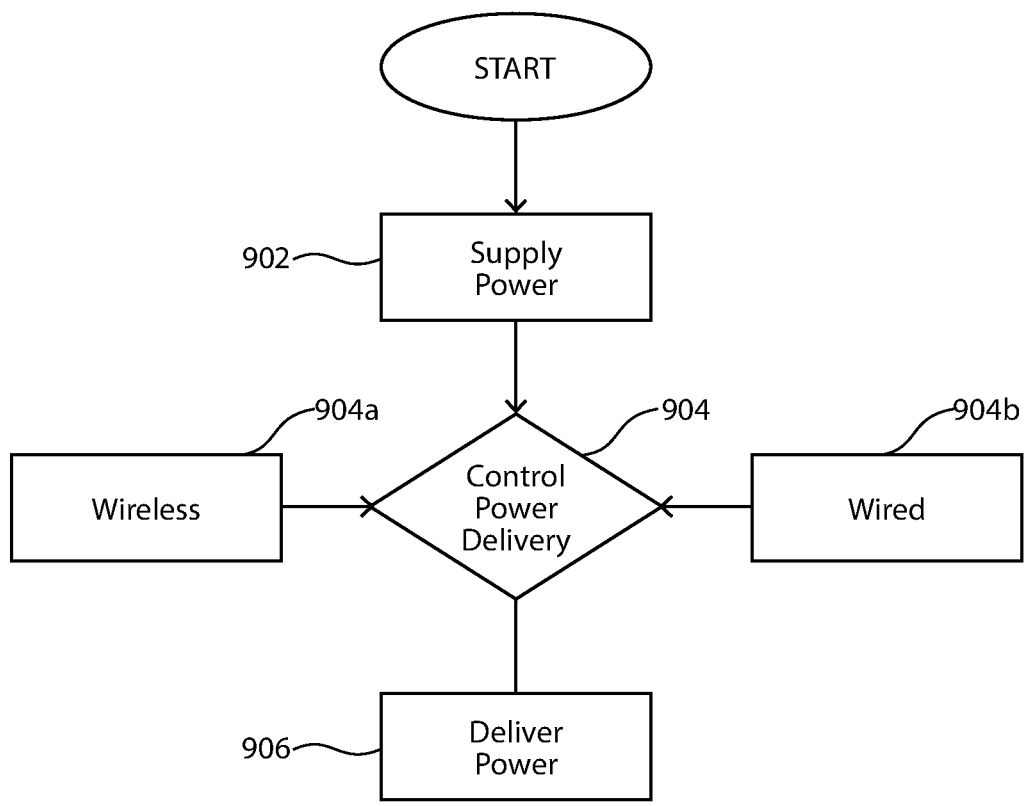
FIG. 9 is a flow diagram illustrating a method of using a conformable heater system within a wearable.

FIG. 9 is a flow diagram illustrating a method 900 of using a conformable heater system. In the illustration, the conformable heater may be associated with a power source at step 902. This association may include a permanent association, such as via recharging of a permanently embedded battery, or a removable association, such as wherein an external power source, such as a battery, a mobile device, or the like, may be removably associated with the heater.

At step 904, the driver circuit that delivers power from the power source to the heater may be variably controlled. Optionally, at step 904a, wireless control may be via a wireless connection, such as from a mobile device to the driver circuit. This wireless, or a wired, connection may be controllable using a user interface provided by an "app" on the mobile device, by way of non-limiting example. The control provided thereby may be automated based on pre-determined triggers or operational limitations, manual, or a combination thereof. Wireless control may be provided over any known type of wireless interface.

Optionally, at step 904b, wired control may be via a wired connection from a mobile device to the driver circuit, such as via a micro-USB connection to the heater. As will be understood by the skilled artisan, power may also be supplied via this connection in alternative embodiments.

Figure 10:
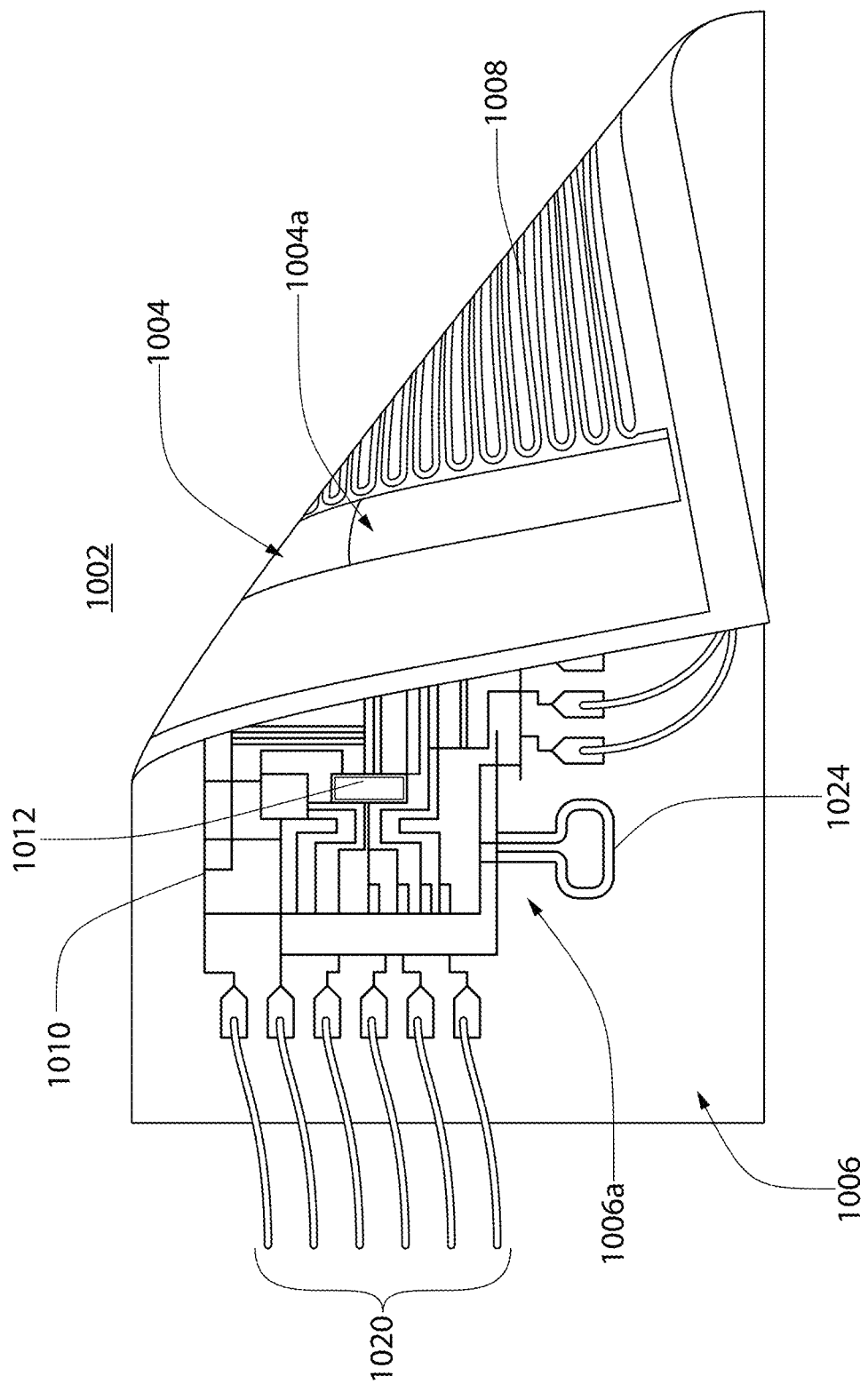
FIG. 10 is an illustration of an exemplary sensing circuit.

FIG. 10 illustrates an exemplary heater base, such as a fluid bag 1002, such as a medical fluid bag 1002, for fully containing one or more fluids within the bag between opposing plies 1004, 1006 of the bag. The fluid contained within the bag may be, for example, blood or saline solution. Of course, in embodiments, other fluids or gases may reside within the "bag", such as air in a wearables embodiment. The plies 1004, 1006 may be sealed together to form a liquid (and/or gas) tight bag via any methodology known in the art.

In the illustrated embodiment, one ply 1004 of the bag may have a printed heater 1008 associated therewith, as discussed throughout, on an outward facing aspect 1004a of that first ply 1004 of the bag, and a sensing circuit 1010 comprising a sensing chip 1012 printed on an outward face 1006a of the opposing ply 1006 of the fluid bag. In the illustrated embodiment, the IC chip 1012 may be a temperature sensor, the sensing circuit 1010 may be a temperature sensing circuit, and the sensing circuit 1010 may include one or more inputs and outputs 1020 that may read data, write data, and/or connectively associate with power and/or with at least one network, such as via wired or wireless interface.

In the illustrated embodiment, either or both of the heating circuit 1008 and the sensing circuit 1010 may be printed circuits, and may be printed directly onto the fluid bag 1002, or may be printed on a separate substrate (not shown) that is then adhered to the fluid bag 1002, such as by lamination or epoxy. Associated with the sensing circuit side 1006a of the fluid bag 1002 may be a printed antenna 1024, such as an RFID or NFC antenna, by way of non-limiting example, and the printed sensing circuit 1010 may include one or more chip sets 1012, or may include one or more inputs or outputs from or to one or more off-bag chip sets.

The sensor circuit 1010 provided may be a printed fluid level sensor circuit, by way of non-limiting example. Alternatively, the sensor circuit 1010 provided may be one or more printed or laminated temperature sensor circuits, by way of non-limiting example. Yet further, the printed sensor circuit 1010 provided may be a combination temperature sensor and level sensing circuit, which may or may not be associated with one or more other sensing circuits for sensing additional characteristics of fluid within the bag 1002.

The sensing circuit 1010 may be communicatively associated, such as via one or more networks and network connections (such as using antenna 1024), with one or more off-bag "apps" or applications, which may provide a human machine interface into data sensed by the printed sensing circuit 1010. This app or application may be provided, by way of nonlimiting example, on one or more mobile devices, desktop or laptop computers, dedicated medical monitoring consoles, or the like. Data may be provided from the sensing circuit 1010 to the one or more applications by a wire or wirelessly, such as using the printed RF or NFC antenna 1024 discussed above.

Figure 11A:
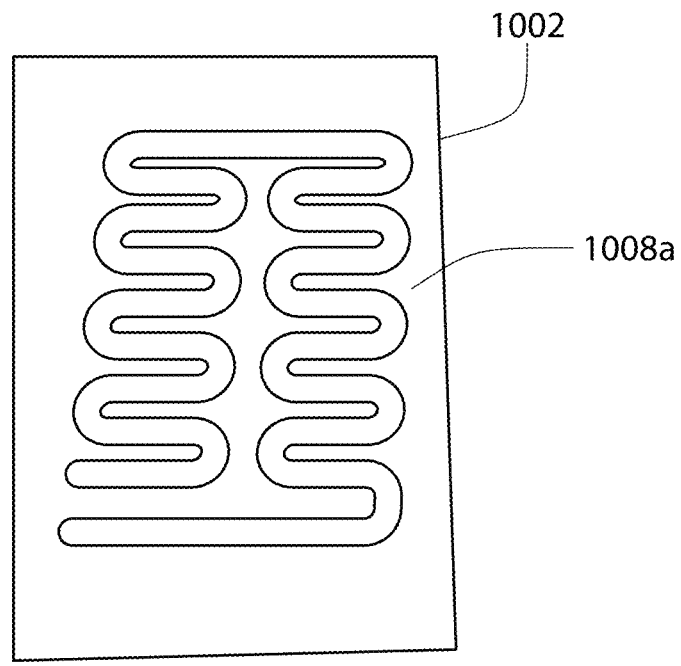
FIGS. 11A-11D are illustrations of exemplary heating circuits.
Figure 11B:
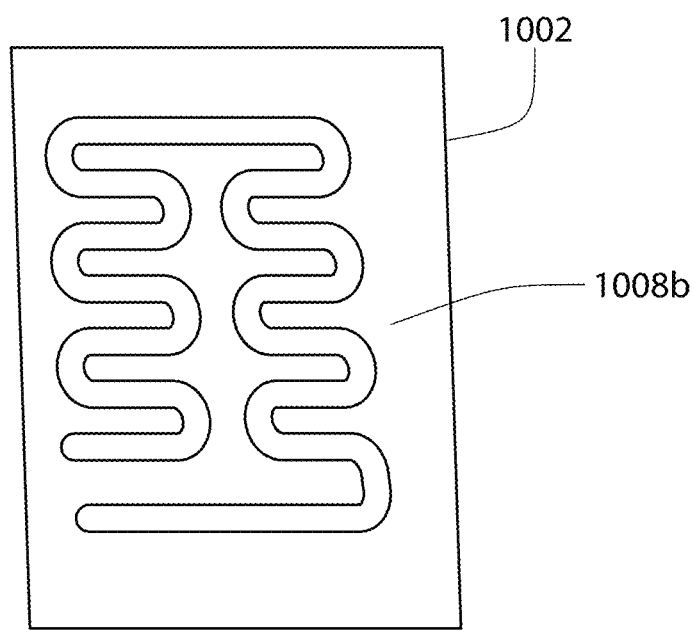
Figure 11C:
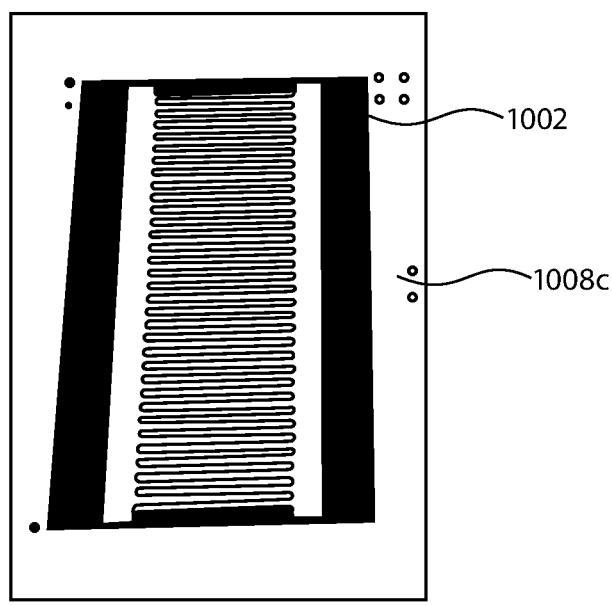
Figure 11D:
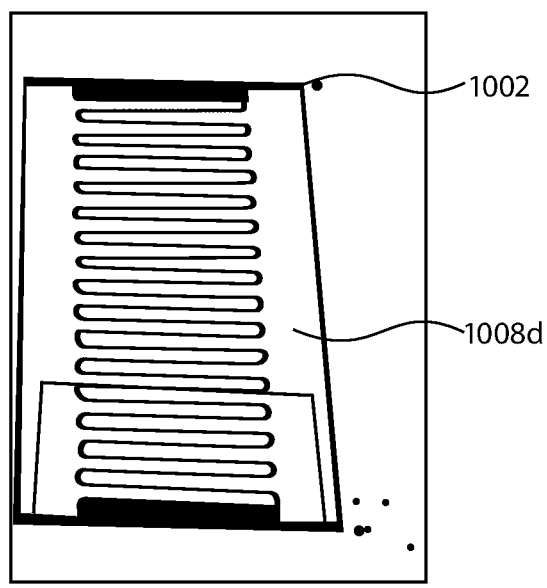

FIGS. 11A, 11B, 11C and 11D illustrate a plurality of alternative printed heater data circuit designs 1008a, 1008b, 1008c, 1008d for physical association with one ply 1006 of the fluid bag 1002. More particularly, FIGS. 11A and 11B illustrate circuit designs 1008a, 1008b for fixed resistance heaters, while FIGS. 11C and 11D illustrate exemplary circuit designs 1008c, 1008d for so-called "railroad pattern" heaters in which even heating and self-limiting temperature are provided. As discussed throughout, the printed heater 1008 may be directly associated with a printed layer on the bag, such as a base resistive layer, or may be printed on a substrate which is associated with a bag after printing of the heater. In either of said circumstances, various inks apparent to those skilled in the art may be employed for use in the heater 1008 and/or in the sensor circuit 1010, such as Henkel PTC 120° C. carbon for the resistive layer, EMS CL-1036 Silver for the conductive layer, and Henkel PF 455B Green for the dielectric layer, by way of nonlimiting example. Further and as will be understood, the printing processes performed in the embodiments may necessarily include drying, pre-shrinking, and/or curing steps, such as UV curing steps, as will be apparent to the skilled artisan in light of the discussion herein.

Figure 12:
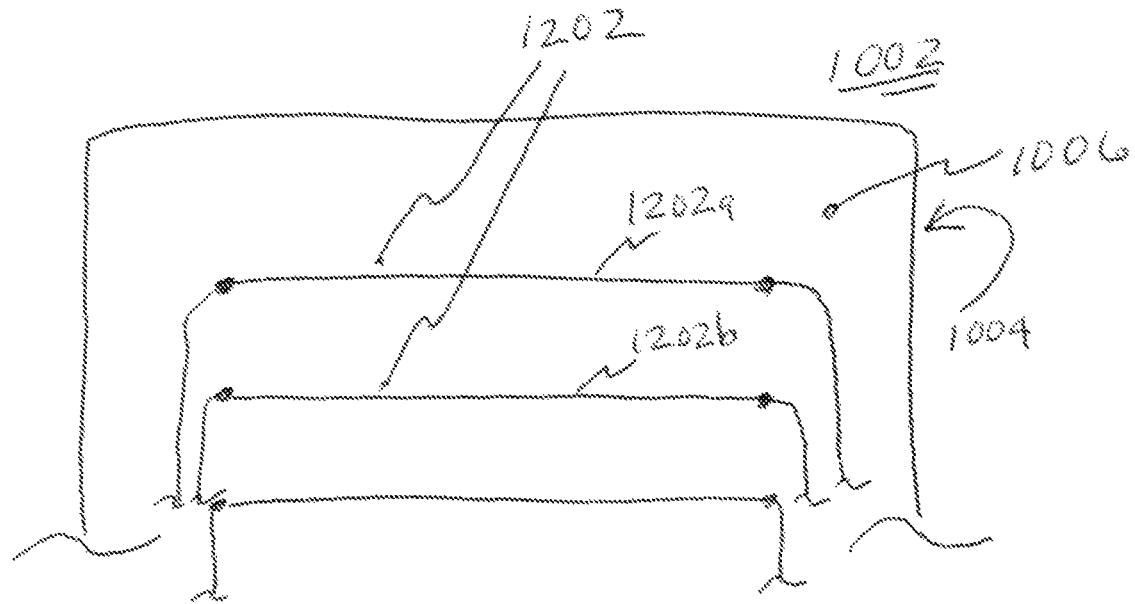
FIG. 12 is an illustration of an exemplary sensing circuit.
Figure 12:
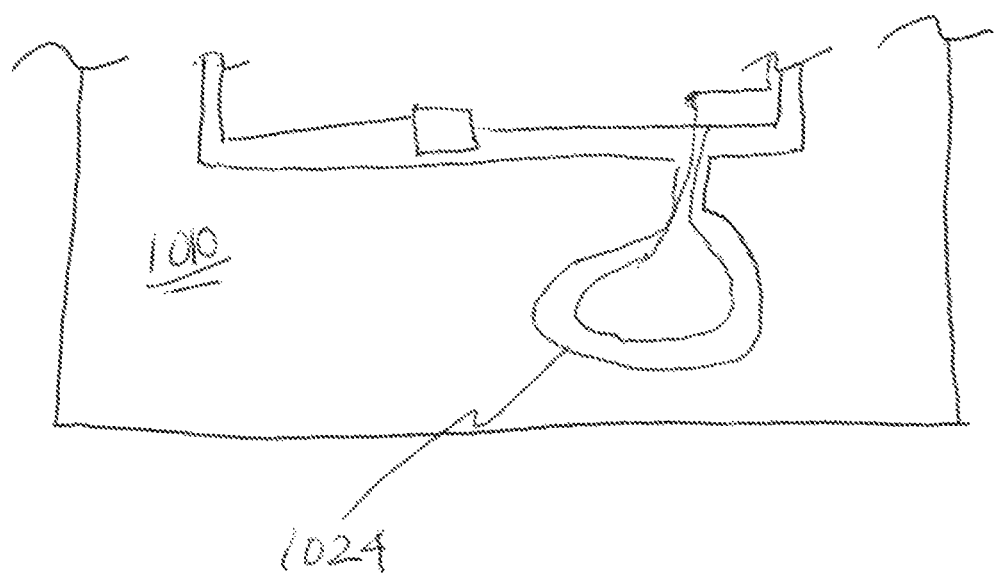

FIG. 12 is an exemplary illustration of a sensor (and data logging/sending circuit 1010 that may be printed on a ply 1006 of the bag that opposes the heating ply 1004. In the illustration of FIG. 12, a thermocouple circuit 1202 may be printed directly onto the bag 1002 and/or otherwise bonded to the bag 1002, such as using conductive epoxy, in order to partially provide a temperature sensing circuit 1010. More particularly, carbon strips 1202a, 1202b, . . . may be screen printed onto the bag and conductively bonded to lead wires that lead off-bag and allow for reading of the temperature of fluid within the bag 1002. Of note, for the embodiment illustrated in FIG. 12 and other sensing embodiments discussed herein, each off-bag data "reading" system may be associated with a single medical bag, or multiple fluid bags, wherein multiple fluid bags may be read, and accordingly data received therefrom, by a single "master" reading device which may then provide output data of the sensing to the human machine interface application discussed throughout.

Figure 13A:
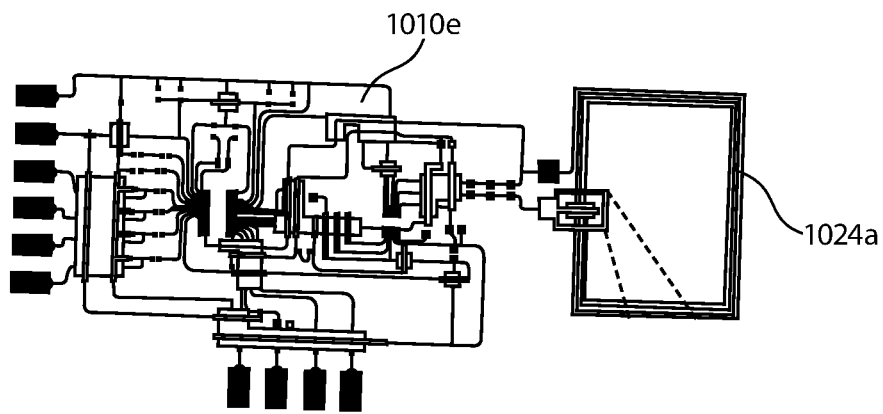
FIGS. 13A-13B are illustrations of exemplary sensing circuits.
Figure 13B:
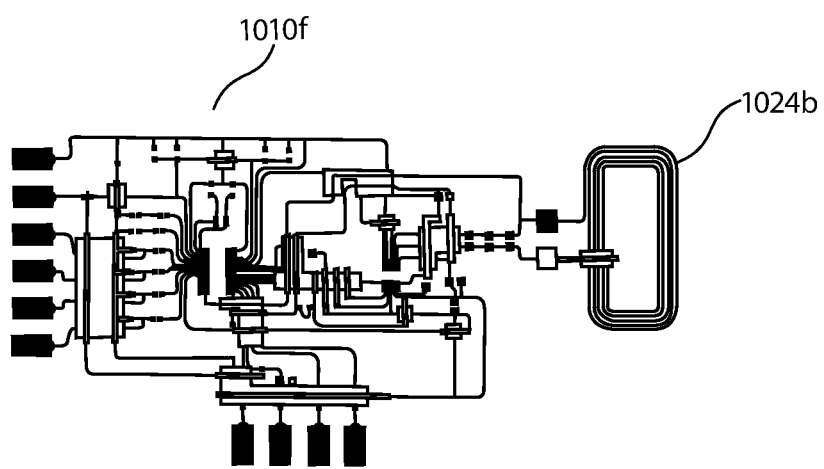

In an alternative embodiment, FIGS. 13A and 13B illustrate printed circuit layouts for sensor circuits 1010e, 1010f for association with a fluid bag 1002. In each illustration, silver ink may be used for, foe example, two different conductive layers, and as shown designs for sensor circuits 1010e, 1010f may include two different dielectric layers which may comprise two different printed inks. Also included in the illustration are two alternative antennas 1024a, 1024b that allow for the illustrated sensing circuits 1010e, 1010f to communicate off-bag.

Significantly, as discussed throughout, and as illustrated with particularity in FIGS. 13A and 13B, the sensor circuit 1010e, 1010f may be printed to the bag 1002 layer by layer. Accordingly, the sensor circuit 1010 of the embodiments comprises an ink set having particular characteristics, both in relation to the bag 1002 or print substrate, and in relation to the other inks within the ink set.

By way of nonlimiting example, these characteristics may include at least the ability for any ink layer that must be associated with the bag to be comprised of an ink suitable to grip to the material of which the bag is constituted. Alternatively, the base layer/substrate of the sensing circuit print may be suitable to associate with an epoxy that will also permanently adhere to the outer surface of the bag ply. Additionally, each successive layer of ink must adhere in the proper manner to both the ink layer below and, in circumstances where necessary, the ink layer to be provided above that sequential layer.

Further, environmental factors must not adversely affect the performance of each layer of the ink set. For example, bag "sweat", i.e., condensation, must not adversely affect any ink that will be printed or adhered in direct physical contact with the bag. Further, external factors must not affect the electrical interaction between layers to cause any undesired electrical interference or interaction. Of course, one or more protection layers may be printed over or below the circuit or any layer of the circuit, but, in the same manner as is discussed above, such protective layers must comport with each layer of the ink set placed below and above, and must not cause unwanted interactions or circuit decay. In particular embodiments, ink sets may include any of a variety of dielectric inks, such as those discussed throughout, and conductive ink layers, such as the copper and silver inks discussed throughout.

In the illustration of FIGS. 13, print widths may be carefully monitored and controlled, such as will be apparent to the skilled artisan in light of the discussion herein. For example, conductive, i.e., silver, trace widths may vary in accordance with Table 1, provided immediately below:

TABLE 1

| Area | Screen Design (μm) | Actual Width (μm) | Printed width (μm) | Percent spread |
|---|---|---|---|---|
| Antenna | 635 | 616.63 ± 4 | 646.26 ± 5 | 4.8% |
| Large | 500 | 485.26 ± 9 | 508.97 ± 7 | 4.9% |
| Small | 250 | 239.44 ± 5 | 266.30 ± 6 | 2.9% |

FIGS. 14A, 14B, and 14C illustrate, by way of nonlimiting example, a human machine interface app/application 1402 as discussed throughout. In the application illustrated in FIGS. 14, the application is associated with a mobile device 1404, such as a smart phone. As shown, the sensing circuit in the illustrated embodiment is a temperature sensing circuit, and a user may have a variety of options available to start, stop, clear, or reset the temperature sensing in association with one or more fluid bags. Other options may additionally be available to the user, such as changes in temperature measurement, a history of measurements over a given time period, such as may be a searchable time period, and the like. Further, and as illustrated with particularity in FIGS. 14B and 14C, temperature data may be provided in numeric format, or graphically, by way of nonlimiting example, and over one or more predetermined or selected time frames.

As will be appreciated by the skilled artisan, rather than associate particular filtering with the printed sensing circuit or firmware discussed herein, adjustment algorithms may be included in the application illustrated in FIG. 14, or in similar off-bag, remote, and/or human machine interface applications. For example, adjustment algorithms may account for the thickness or makeup of particular brands of fluid bags, particular heating circuits that may be associated with the fluid bag, or the like, by way of nonlimiting example.

Figure 15:
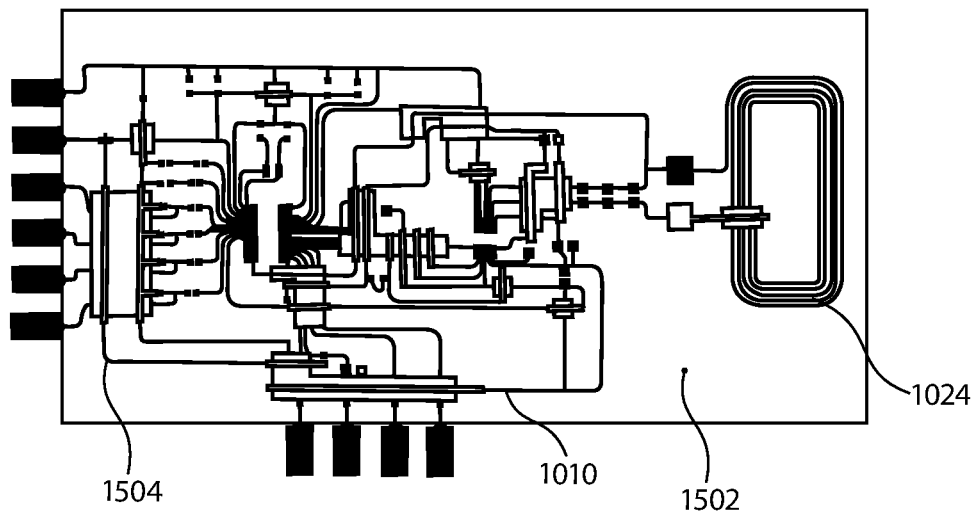
FIG. 15 is an illustration of an exemplary sensing circuit.
Figure 16:
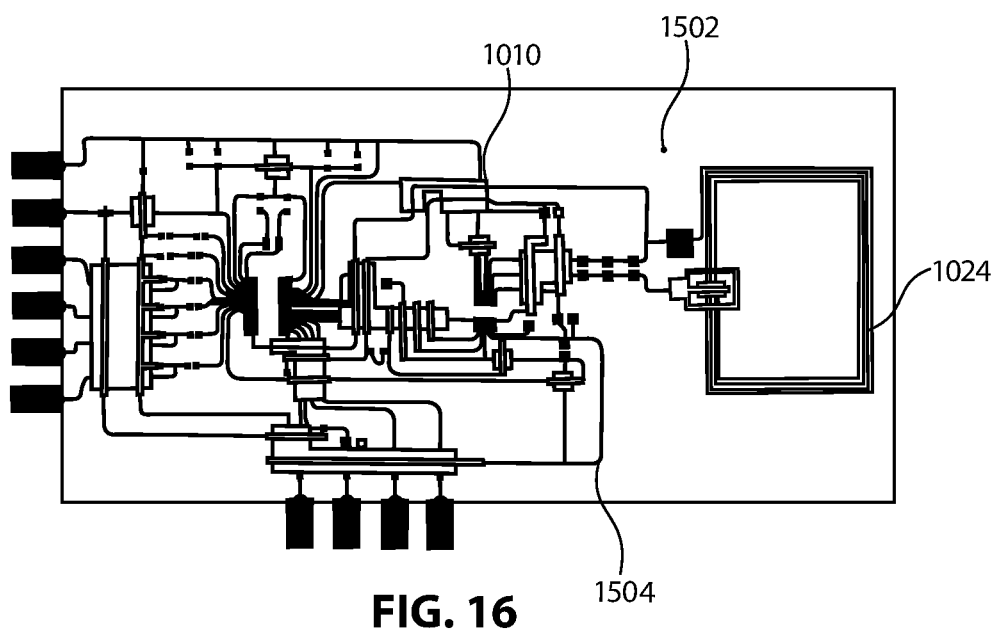
FIG. 16 is an illustration of an exemplary sensing circuit.

As discussed throughout, and as illustrated in FIGS. 15 and 16, one or more additional protective layers 1502 may be provided over the sensing circuit 1010. Such protective outermost layers may be similar to those discussed above with respect to protecting a heating circuit printed on the other ply of the bag. Such a protective layer 1502 may be formed of a dielectric, by way of nonlimiting example, and may thereby prevent oxidation of the conductive layers 1504 of the sensing circuit, may protect the circuit, traces, and electrical connections from physical damage, and may reinforce the proper conductive nature of the traces, particularly at the edges of encapsulated areas.

Figure 17A:
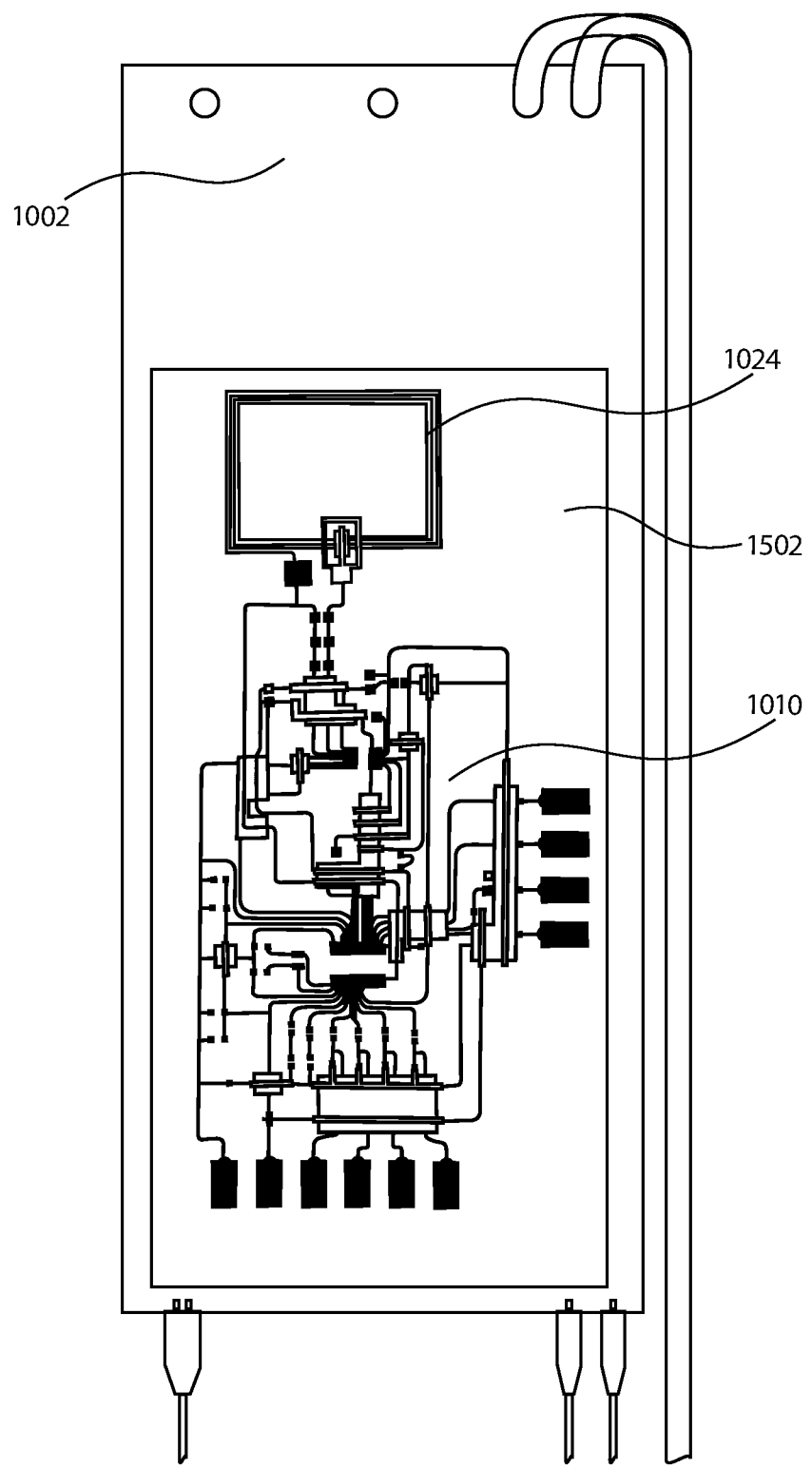
FIGS. 17A-17C are illustrations of exemplary sensing circuits.
Figure 17B:
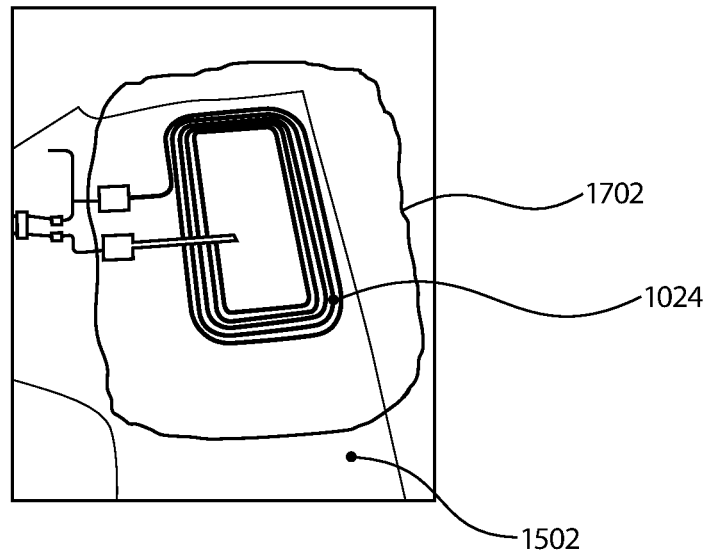
Figure 17C:
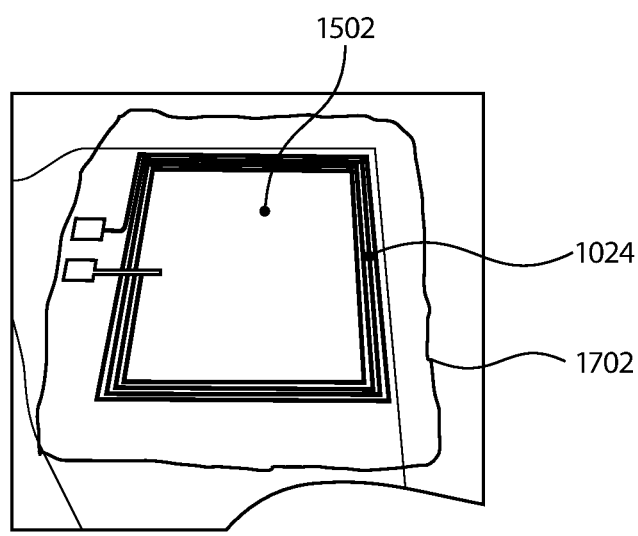

More particularly, specific and/or more extensive protective printed layers may be provided in association with particularly delicate portions of the printed sensing circuit, and/or in association with particularly complex applications for circuit 1010. By way of example, because of variations in bag curvature when an intravenous (IV) bag is filled versus empty, a more rigid secondary under layer or cover layer 1702 may be provided in association with the printed antenna 1024 of the sensing circuit 1010. This may keep the antenna 1024 as flat as possible, thereby maximizing communication integrity and read range for the printed sensing circuit 1010. Such embodiments are illustrated, by way of nonlimiting example, in FIGS. 17A, 17B and 17C.

In addition to the temperature sensing circuit discussed throughout, also referenced above is a fluid level sensing circuit. Such a circuit may monitor fluid levels within the bag and may thereby allow for automated indications of the need for bag replacement and the like. Such sensing, although not illustrated with particularity herein, may have access thereto also provided through the human machine interface application discussed throughout.

A fluid level sensing circuit may comprise, by way of example, a self-capacitive sensing circuit, such as may include a plurality of silver traces used to measure bag capacitance at various locations across the bag. Additionally and alternatively, rather than capacitive strips, capacitor buttons may be placed along particular areas of a ply of the fluid bag. Each button may act as a capacitive detector to indicate whether the fluid has reached that level. Of course, other methods of printing level sensing circuits, such as capacitive level sensors, will be apparent to those skilled in the art in light of the discussion herein and may be subjected to the ink set limitations discussed throughout.

By way of nonlimiting example, a sensing circuit 1010 may include one or more conductive inks, such as EMS CL-1036 Silver ink, and one or more dielectric layer inks, such as EMS DL-7540 Blue. Conductive adhesives for certain of the layers may be comprised of any conductive adhesive known to those skilled in the art for incorporation into the instant embodiments, such as Henkel QML516LE, Henkel 2030 SC, and Henkel SL-5421. The encapsulating layer may be comprised of any known principle material, such as laminate VE 529610.

Further, the descriptions of the disclosure are provided to enable any person skilled in the art to make or use the disclosed embodiments. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but rather is to be accorded the widest scope consistent with the principles and novel features disclosed herein.

What is claimed is:

1. A flexible heater sensor suitable for external association with a fluid bag, comprising:
a conformable substrate on a ply of the fluid bag opposite a printed flexible heater;
a matched function ink set, printed onto at least one substantially planar face of the substrate to form:

at least one conductive layer capable of receiving current flow from at least one power source; and at least one dielectric layer capable of at least partially insulating and at least partially limiting conductivity of the at least one conductive layer;

wherein the matched ink set is matched to preclude detrimental interactions between the printed inks of each of the at least one conductive and dielectric layers, and to preclude detrimental interactions with the conformable substrate, based on at least one of a compatibility of the substrate, a receptivity the substrate, a conductivity of the inks, a type of printing method performed, a thickness of the printed layers, a chemical reaction between the inks, a curing methodology of the inks, a manner of deposition of the inks, and a surface energy of the substrate; and wherein the at least one conductive layer and the at least one dielectric layer comprise a sensing circuit that senses at least the temperature of fluid within the fluid bag.

2. The flexible heater sensor of claim 1, wherein the substrate comprises an inorganic substrate.

3. The flexible heater sensor of claim 1, wherein the substrate comprises one selected from the group consisting of PET, PC, TPU, nylon, glass, fabric, PEN, and ceramic.

4. The flexible heater sensor of claim 1, wherein the printed inks in the matched ink set include ones selected from the group consisting of silver, carbon, PEDOT:PSS, and CNT inks.

5. The flexible heater sensor of claim 1, wherein the printed ink set withstands moisture.

6. The flexible heater sensor of claim 1, further comprising an encapsulation that at least partially seals at least the conformable substrate having the matched function ink set thereon from environmental factors.

7. The flexible heater sensor of claim 6, wherein the encapsulation comprises a lamination.

8. The flexible heater sensor of claim 1, wherein the sensing circuit also senses the fluid level of the fluid in the fluid bag.

9. The flexible heater sensor of claim 8, wherein the fluid level sensing comprises a plurality of capacitive strips.

10. The flexible heater sensor of claim 1, wherein the conformable substrate comprises the ply.

11. The flexible heater sensor of claim 1, wherein the conformable substrate is adhered to the ply.

12. The flexible heater sensor of claim 1, wherein the sensing circuit comprises a wireless sender.

13. The flexible heater sensor of claim 12, wherein the wireless sender comprises at least one of a Bluetooth, WiFi, NFC, cellular and RF sender.

14. The flexible heater sensor of claim 12, wherein the wireless sender interacts data from the sensing circuit to a remote mobile device app.

15. The flexible heater sensor of claim 14, wherein the mobile device app is configured to account for at least one of a type of the fluid bag, a bag material thickness, and a bag material makeup.

16. The flexible heater sensor of claim 1, wherein the power source comprises a rechargeable battery.

17. The flexible heater sensor of claim 1, wherein the dielectric layer insulates at least a portion of of the conductive layers from shorting onto one another due to the conformability of the conformable substrate.

18. The flexible heater sensor of claim 1, wherein ones of the dielectric layers comprise reinforcement layers.

19. The flexible heater sensor of claim 1, wherein the fluid bag is an IV bag.

* * * * *